United States Patent [19]

Bennett

[11] Patent Number: Plant 6,456

[45] Date of Patent: Dec. 13, 1988

[54] MINIATURE ROSE PLANT 'CHEER UP'

[76] Inventor: Cecilia L. D. Bennett, 489 Minot Ave., Chula Vista, Calif. 92010

[21] Appl. No.: 10,826

[22] Filed: Feb. 4, 1987

[51] Int. Cl.[4] ..... A01H 5/00

[52] U.S. Cl. ..... Plt./10

[58] Field of Search ..... Plt./10

*Primary Examiner*—James R. Feyrer

[57] ABSTRACT

The subject of the present disclosure is a new and distinct variety of miniature rose plant, named 'Cheer Up', which is characterized by its bright orange-red blooms, ranging from Mandarin Red to Capsicum Red, usually one to a stem with hybrid tea form. The bush is vigorous, well-branched and produces moderate to heavy quantities of bloom.

1 Drawing Sheet

The present invention relates to a new and distinct variety of a hardy, dwarf, bush plant of the miniature class; the variety being primarily characterized as an orange-red.

The variety is further characterized by:

Long stemmed blooms of hybrid tea-type form, borne usually one to a stem but on occasion in sprays of 3 to 5 or more. The blooms are held very erect and well above the foliage.

It has a slight fragrance.

The plant ranges in height from 24 to 36 inches (approximately 60 to 90 cm). The canes are sturdy and erect with moderate branching and medium to heavy foliage covering. The plant is a moderate to heavy bloomer that does well either in the green house or outdoors.

The plant has good growth habits, well-shaped and attractive, bearing numerous leaflets of average size.

The seed parent was Futura (U.S. Plant Pat. No. 3,569), and the pollen parent was Bread 'n Butter (miniature rose plant, orange blend; Cecilia Bennett; introduced by Tiny Petals Nursery, 1985). It differs from its seed parent in the following ways. It is a miniature rose with appropriately small bloom size (3 to 4 cm) and plant height (24 to 36 inches), and Futura is a hybrid tea rose with blooms of 10 to 12 cm and a plant height in excess of 5 feet. It differs from its pollen parent in the following ways. It is an orange-red, and Bread 'n Butter is an orange blend with softer tones of orange and yellow blending and reverse.

The descriptive matter which follows pertains to roses grown and color values observed in plants and newly opened blooms in the months March through August 1986. The plants were grown outdoors in Chula Vista, Calif., and are believed to be accurate standards for this cultivar in similar conditions of soil and climate elsewhere.

The color photograph illustrates the variety.

Referring now specifically to the new and distinct variety of miniature rose plant named 'Cheer Up', the following is a detailed description thereof in outline; all major color plate identifications being by reference to the British Colour Council Horticultural Colour Chart, except where common terms of color definition are employed.

Type: Hardy, upright, spreading, green house or outdoor, decorative and exhibition potted plant.

Class: Miniature.

Variety name: CHEER UP

Flowers borne: Usually one to a stem, but occasionally in sprays of 3 to 5 or more on erect stems with foliage well below the blooms.

Quantity of bloom: Moderate to heavy both outdoors or green house grown.

Bud:

*Peduncle.*—Variable in length (30 to 40 mm); average diameter and sturdy; ranging in color from near Scheeles Green (860/3 to 860/2 page 175) to near Lettuce Green (861/2 to 861/1 page 176) with some tinting of bronze.

*Hairs.*—Extremely small and numerous with a reddish color; located over the entire surface of the peduncle and sepals, but not present on the calyx tube.

*Calyx.*—Color ranging from near Scheeles Green (860/3 to 860/2 page 175) to near Lettuce Green (861/2 to 861/1 page 176).

*Opening.*—Opens well in all weather.

Bloom:

*Size when fully open.*—Average for a miniature variety (30 to 40 mm).

*Petalage.*—Full — Averaging 25 to 30 petals, arranged regularly, plus petaloids (3 to 5 or more).

*Form.*—Urn-shaped to ovoid as the bloom progresses. The petals remain at first somewhat tightly cupped with the apex and/or margins reflexed outward, becoming at maturity more loosely cupped; and the petals reflex more tightly (quilling), until each row of petals forms a five-pointed star.

Petals: Fairly thick with good substance; both the upper and under surfaces of all petals have a matte finish.

*Shape.*—Outer petals are of a very broad obovate form. The intermediate petals are very much like the outer petals only narrower. The inner petals are a broad lanceolate form; and the petaloids are also lanceolate form with some occasional irregularities.

Color: Newly opened flowers from plants grown outdoors (March through August 1986), Chula Vista, Calif.

*All petals.*—Upper and under surfaces — Ranging from near Mandarin Red (17/1 to 17 page 17) to near Capsicum Red (715/2 to 715/1 page 715) with a tip of near Mimosa Yellow (602/1 to 602 page 602).

*General color effect.*—Newly opened flower — Bright orange-red with only a slight fading of the outer petals as the bloom opens. to

*Flower longevity.*—(March to August 1986) Plant in pot 5 to 7 days from bud with sepals reflexed to fully opened bloom. Holding at fully opened with slight fading of the color for 3 to 5 days or longer. Cut blooms at living room temperature 4 to 7 days or longer.

Reproductive organs:

*Stamens.*—A generous amount arranged uniformly around the pistil.

*Filaments.*—Varying in length with shorter filaments more proximal to the pistil; golden yellow including the anthers.

*Pollen.*—Abundant.

*Pistil.*—Long, abundant and spreading; pale yellow at the base to reddish at the top with pale yellow caps on the styles.

*Ovaries.*—All encased in calyx.

*Hips.*—Some.

*Seeds.*—3 to 5 or more in each hip.

*Sepals.*—Permanent; spear-shaped; open as the bloom opens; recurving against the peduncle, when the bloom is fully opened.

Foliage:

*Leaves.*—Five to seven leaflets on the average; medium size for a miniature rose plant.

*Leaflets.*—Broad ovate-shaped.

*Margin.*—Very serrated with tinting of bronze, especially noticeable on the newer foliage.

*Color.*—Ranging from near Spinach Green (0960/3 to 0960/2 page 175) to near Lettuce Green (861/1 to 861 page 176) with occasional bronzing of the margins, especially noticeable on the newer foliage. Upper surfaces have a semi-glossy finish, and the under surfaces have a matte finish of a slightly lighter shade than the upper surfaces.

*Rachis.*—Medium strength; upper surface is grooved with very small hairs over the length of it. Under surface has few if any hairs but does contain 2 to 5 small thorns.

*Stipules.*—Varying in length from small to medium; average width; tapering auricles angled outward at about 45 degrees.

Growth:

*Habit.*—Upright and spreading; average to tall height for a miniature rose plant.

*Growth.*—Vigorous and well-branched.

*Canes.*—Medium diameter; sturdy; held erect.

*Main stems.*—Color — Ranging from near Scheeles Green (0960/3 to 0960/2 page 175) to near Lettuce Green (861/1 to 861 page 861).

*Thorns.*—Averaging 25 to 30 per 10 cm on the main stems and fewer on the branches. Reddish in color, especially on the newer branches. Small to average in size. Slender and straight.

*Branches.*—Color — Same as main stems.

I have found this variety to be easily asexually reproduced from cuttings, with flowers borne usually one to a stem but occasionally in sprays of 3 to 5 or more.

The miniature rose plant and its flowers as herein described may vary in slight detail due to climate, soil and cultural conditions under which the variety may be grown; the present description being of the variety as grown at Chula Vista, Calif.

The following is claimed:

1. A new and distinct variety of miniature rose plant named, 'Cheer Up' of hardy, dwarf, vigorous growth, well-branched and attractive in appearance, substantially as illustrated and described, characterized by its blooms of bright orange-red, ranging from near Mandarin Red to near Capsicum Red.

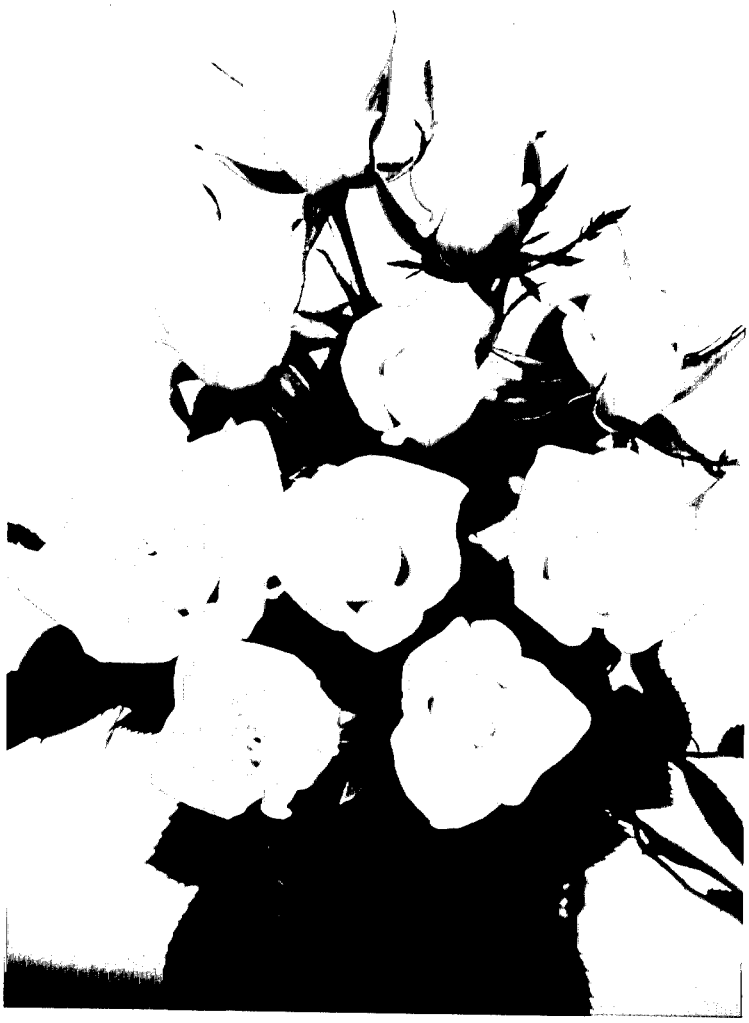

* * * * *